United States Patent

Rosseels et al.

[11] Patent Number: 4,499,095
[45] Date of Patent: Feb. 12, 1985

[54] INDOLIZINE DERIVATIVES AND THEIR USE IN TREATING HEART AILMENTS

[75] Inventors: Gilbert Rosseels, Wemmel; Peter Polster, Hamme-Mille, both of Belgium

[73] Assignee: Sanofi, Paris, France

[21] Appl. No.: 501,856

[22] Filed: Jun. 7, 1983

[30] Foreign Application Priority Data

Jun. 17, 1982 [FR] France .................. 82 10598

[51] Int. Cl.³ .................... A61K 31/44; C07D 471/04
[52] U.S. Cl. .................... 514/299; 546/112; 546/183
[58] Field of Search ............... 546/112, 183; 424/256

[56] References Cited

U.S. PATENT DOCUMENTS 4,103,012 7/1978 Gubin et al. ................ 546/112
4,378,362 3/1983 Rosseels et al. ............ 546/112

Primary Examiner—Henry R. Jiles
Assistant Examiner—Bernard I. Dentz
Attorney, Agent, or Firm—Bacon & Thomas

[57] ABSTRACT

Indolizine derivatives corresponding to the general formula:

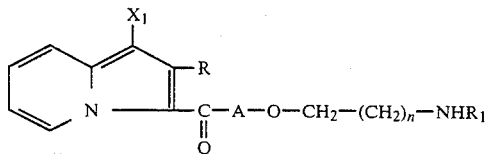

and the pharmaceutically acceptable acid addition salts thereof, wherein: R represents a straight- or branched-chain alkyl radical having from 1 to 4 carbon atoms or a phenyl radical, $R_1$ represents a straight- or branched-chain alkyl radical having from 1 to 6 carbon atoms, $X_1$ represents hydrogen, chlorine, bromine, methyl or methoxy, A represents a radical of the formula:

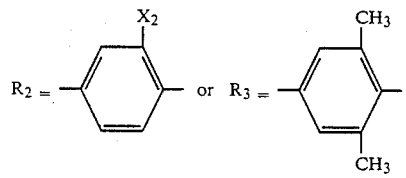

in which $X_2$ represents hydrogen, chlorine, bromine, methyl or methoxy, n represents 1 or 2, a process for preparing said derivatives, pharmaceutical or veterinary compositions containing at least one of said derivatives and a method of treating pathological syndromes of the heart by administration of at least one of said derivatives to a subject in need of such treatment.

13 Claims, No Drawings

INDOLIZINE DERIVATIVES AND THEIR USE IN TREATING HEART AILMENTS

This invention relates to heterocyclic compounds and is concerned with novel indolizine derivatives and with a process for preparing the said novel derivatives.

The indolizine derivatives with which the present invention is concerned are the compounds represented by the general formula:

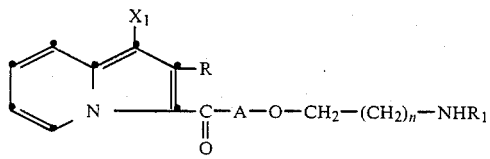

in which:

R represents a straight- or branched- chain alkyl radical having from 1 to 4 carbon atoms or a phenyl radical, $R_1$ represents a straight- or branched-chain alkyl radical having from 1 to 6 carbon atoms, $X_1$ represents hydrogen, chlorine, bromine, methyl or methoxy, A represents a radical of the formula:

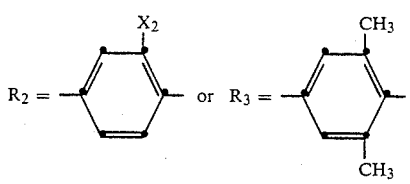

in which $X_2$ represents hydrogen, chlorine, bromine, methyl or methoxy in represents 1 or 2.

The invention also relates to the pharmaceutically acceptable acid addition salts of the compounds of formula I, for instance the hydrochloride, hydrobromide or oxalate.

In the aforesaid formula I, R can represent a methyl, ethyl, n-propyl, isopropyl, n-butyl, isobutyl or tert-butyl radical, $R_1$ can represent a methyl, ethyl, n-propyl, isopropyl, n-butyl, isobutyl, tert-butyl, n-pentyl, isopentyl or neopentyl radical.

Furthermore, preferred compounds of formula I are those in which $R_1$ represents a branched-chain alkyl radical, for example tert-butyl or neopentyl. The indolizine derivatives of the invention have been found to possess useful pharmacological properties, and more particularly that they are capable of inhibiting calcium translocation at the level of the cell membrane.

These properties are likely to render the compounds in question of considerable value in the treatment of certain pathological syndromes of the heart, and more particularly in the treatment of angina pectoris, hypertension, arrhythmias and cerebral circulatory insufficiency. In the anti-tumor field, the compounds of the invention may be useful as a means of potentiating the activity of anticancer agents.

Yet, another object of the invention relates to pharmaceutical or veterinary compositions containing, as active principle, at least one indolizine derivative of formula I or a pharmaceutically acceptable acid addition salt thereof, in association with a pharmaceutical carrier or excipient therefor.

A further object of the invention relates to a method of treating pathological syndromes of the heart comprising the administration of an effective dose of at least one indolizine derivative of the invention.

Depending on the route of administration selected, the daily dosage for a human being weighing 60 kg will be from 2 to 500 mg of active principle. The compounds of formula I can be prepared, in accordance with the invention, by condensing in an inert medium such as, for example, benzene or toluene, a bromoalkoxy-benzoyl-indolizine of the general formula:

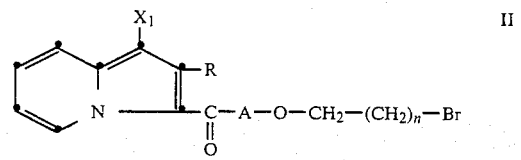

in which R, $X_1$, A and n have the same meaning as in formula I, with a primary amine of general formula:

$$H_2N-R_1 \qquad \text{III}$$

in which $R_1$ has the same meaning as in formula I, to form the required indolizine derivative of formula I which, if desired, is reacted with an appropriate organic or inorganic acid to provide a pharmaceutically acceptable acid addition salt thereon.

Condensation will preferably be carried out at a temperature between room-temperature and 75° C.

The compounds of formula II are known products having been described in British Pat. Nos. 1,518,443 and 2,064,536.

Contemporary medical opinion holds that the pathophysiology of angina pectoris is a spectrum ranging from pure fixed atherosclerotic lesion to pure coronary artery spasm.

Many patients, however, are believed to have a combination of both lesion and spasm.

Angina due to pure fixed lesion can be prevented by reducing oxygen demand. Angina due to coronary artery spasm can be treated by preventing the spasm itself, thereby increasing oxygen supply.

With this new understanding of angina, optimal antianginal therapy should provide this dual action: increasing oxygen supply while reducing oxygen demand.

It is known that calcium ions, working at the cellular level, regulate the degree of vasoconstriction and, thereby, play a critical role in the anginal attack.

The calcium-antagonistic compounds act at the cell membrane to selectively block calcium access to the contractile process in the arterial cell. Through this action, such compounds manage the following pathological phenomena:

vasospastic angina by dilating coronary arteries to increase myocardial oxygen supply and preventing coronary artery spasm effort-associated angina by dilating peripheral arteries to reduce afterload and myocardial oxygen demand mixed angina which involves elements of vasospastic and effort-associated angina.

Amongst the products used in the long-lasting prevention of angina can be cited the β-receptor blocking agents.

These β-blockers prevent angina primarily by lowering myocardial oxygen demand. Like these agents, the calcium antagonists, such as nifedipine, reduce myocardial oxygen demand but provide an added dimension of angina control by increasing myocardial oxygen supply where coronary artery spasm is present.

Furthermore:

the β-blockers can actually cause spasm while the calcium antagonists prevent spasm the β-blockers decrease myocardial perfusion in poststenotic areas while the calcium antagonists increase myocardial perfusion to both normal and poststenotic areas β-blockers treatment is limited in patients with myocardial dysfunction, asthma, bundle branch blocks and diabetes. The calcium antagonists can be given safely in all these groups of patients.

Furthermore, some authors hold that the cardiodepressant action of calcium antagonistic compounds at the myocardial level "in situ" is to a certain extent regulated by a reflex mechanism. This reflex mechanism, of which the main line of action lies through the β-adrenergic system, brings about an increase in the power and rapidity of the cardiac contraction. Thus, whenever there is an excessive drop in arterial pressure, a reflex action is triggered off which liberates endogenous sympathetic transmitters. When this system is blocked a state of cardiac insufficiency is aggravated. This release of catecholamines can partially neutralize the cardiodepressant action of the calcium-antagonists. Unlike the β-adrenergic inhibitors, the calcium-antagonists do not, in fact, inhibit the myocardial response to β-adrenergic catecholamines.

Through this adrenergic compensatory mechanism, the calcium-antagonists unlike the β-adrenergic blocking agents could, therefore, moderate to some degree certain undesirable peripheral phenomena such as a drop in arterial pressure.

An indolizine derivative is already known namely butoprozine or 2-ethyl-3-[4-(3-di-n-butylamino-1-propyl)oxy-benzoyl]-indolizine as presenting both α- and β-antiadrenergic properties i.e. partial inhibitory properties of the α- and β-adrenergic reactions (British Pat. No. 1,518,443) as well as calcium-antagonistic properties (Biochemical Pharmacology, Vol. 30, No. 8, pp. 897–901, 1981).

However, it has been found, in accordance with the invention, that the compounds of formula I as well as their pharmaceutically acceptable acid addition salts are endowed with calcium-antagonistic properties while being devoid of significant antiadrenergic properties at doses at which such properties are observed with butoprozine.

Since the inhibitory action on the adrenergic system of the compounds of the invention, is only very weak or non-existent, it is reasonable to suppose, in accordance with the mechanism described above, that the use of these compounds will be, in many cases, more advantageous than that of butoprozine.

It thus appears that the calcium-antagonists, such as those of the present invention, represent a novel approach for managing angina pectoris particularly in cases where it is preferable not to inhibit the response of the adrenergic system.

The results of pharmacological trials carried out in order to determine the cardiovascular properties of the compounds of the invention are listed below.

I. Calcium-antagonistic properties

The inhibitory properties with respect to calcium translocation at the level of the cellular membrane presented by the compounds of the invention have been determined by measuring their antagonistic action with regard to the contractile response to potassium-induced depolarization on the rat aorta. It is well known that depolarization by potassium of smooth-muscle membrane, renders the latter permeable to extracellular calcium and provokes muscular contraction.

Therefore, measuring the inhibition of the contractile response to potassium-induced depolarization or the tonic contraction to potassium-induced depolarization can constitute a means of evaluating the power of a compound to inhibit cellular membrane permeability to $Ca^{++}$ ions.

The following technique was used:

The thoracic aorta of male rats of the Wistar species weighing about 300 g was removed and cut spirally in strips of about 40 mm long and 3 mm wide. These pieces were placed in a 25 ml-receptacle containing a modified Krebs-bicarbonate solution (NaCl 112 m M; KCl 5 m M; $NaHCO_3$ 25 m M; $KH_2PO_4$ 1 m M; $MgSO_4$ 1.2 m M; $CaCL_2$ 2.5 m M; glucose 11.5 m M; distilled water to 1000 ml). This solution was oxygenated while being maintained at 37° C.

The preparation was linked to an isometric force transducer and the contractile response was registered after being amplified.

A tension of 2 g was applied to the organ which was kept for 60 minutes in the modified Krebs-bicarbonate solution. Contractions were than provoked by replacing the Krebs-bicarbonate solution by a Krebs-potassium solution (NaCl 17 m M; KCl 100 m M; $NaHCO_3$ 25 m M; $KH_2PO_4$ 1 m M; $MgSO_4$ 1.2 m M; $CaCl_2$ 2.5 m M; glucose 11.5 m M; distilled water to 1000 ml). When the contractile response was found to be reproductible, a given does of the compound of the invention was introduced into the bath. Sixty minutes later, a new spasm was provoked by potassium depolarization. The results obtained on each aorta studied were then expressed in % of the maximal contracting effect registered before incubation with the compound to be tested.

Examples of results so obtained are given below:

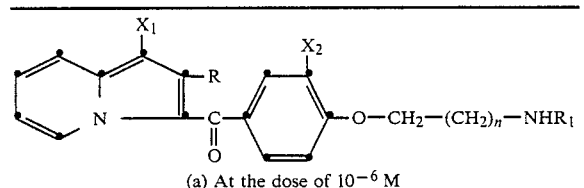

(a) At the dose of $10^{-6}$ M

| R | R₁ | X₁ | X₂ | n | Maximal contracting effect (%) |
|---|---|---|---|---|---|
| (a) At the dose of $10^{-6}$ M | | | | | |
| $CH_3$ | $C-(CH_3)_3$ | H | H | 2 | 59 |
| $C_2H_5$ | $C_2H_5$ | H | H | 2 | 66.2 |
| $C_2H_5$ | $C-(CH_3)_3$ | H | H | 2 | 4.4 |
| $C_2H_5$ | $CH_2-C-(CH_3)_3$ | H | H | 2 | 8.6 |
| $n-C_3H_7$ | $C-(CH_3)_3$ | H | H | 2 | 0 |
| $n-C_3H_7$ | $CH_2-C-(CH_3)_3$ | H | H | 2 | 6.2 |
| $iso-C_3H_7$ | $n-C_4H_9$ | H | H | 2 | 25 |
| $iso-C_3H_7$ | $C-(CH_3)_3$ | H | H | 2 | 4.2 |
| $iso-C_3H_7$ | $C-(CH_3)_3$ | Br | H | 2 | 28.6 |
| $iso-C_3H_7$ | $C-(CH_3)_3$ | H | Br | 2 | 11.4 |
| $n-C_4H_9$ | $C-(CH_3)_3$ | H | H | 1 | 65.3 |
| $n-C_4H_9$ | $CH_2-C-(CH_3)_3$ | H | H | 1 | 40.9 |
| $n-C_4H_9$ | $CH_3$ | H | H | 2 | 69.8 |
| $n-C_4H_9$ | $C_2H_5$ | H | H | 2 | 51.6 |

-continued

| | | | | | |
|---|---|---|---|---|---|
| n-C$_4$H$_9$ | n-C$_3$H$_7$ | H | H | 2 | 29.1 |
| n-C$_4$H$_9$ | iso-C$_3$H$_7$ | H | H | 2 | 33 |
| n-C$_4$H$_9$ | C—(CH$_3$)$_3$ | H | H | 2 | 7.6 |
| n-C$_4$H$_9$ | CH$_2$—C—(CH$_3$)$_3$ | H | H | 2 | 16.4 |
| n-C$_4$H$_9$ | n-C$_4$H$_9$ | Cl | H | 2 | 54.5 |
| n-C$_4$H$_9$ | C—(CH$_3$)$_3$ | Cl | H | 2 | 44.7 |
| n-C$_4$H$_9$ | C—(CH$_3$)$_3$ | Br | H | 1 | 61.4 |
| n-C$_4$H$_9$ | CH$_2$—C—(CH$_3$)$_3$ | Br | H | 1 | 66.2 |
| n-C$_4$H$_9$ | C—(CH$_3$)$_3$ | Br | H | 2 | 45 |
| n-C$_4$H$_9$ | CH$_2$—C—(CH$_3$)$_3$ | Br | H | 2 | 59.8 |
| n-C$_4$H$_9$ | C—(CH$_3$)$_3$ | H | OCH$_3$ | 2 | 3.6 |
| ⌬ | n-C$_4$H$_9$ | H | H | 2 | 57.4 |
| ⌬ | C—(CH$_3$)$_3$ | H | H | 2 | 29.8 |
| Butoprozine | | | | | 6.1 |

(b) At the dose of $10^{-7}$ M

| | | | | | |
|---|---|---|---|---|---|
| C$_2$H$_5$ | C—(CH$_3$)$_3$ | H | H | 2 | 71 |
| C$_2$H$_5$ | CH$_2$—C—(CH$_3$)$_3$ | H | H | 2 | 61.6 |
| iso-C$_3$H$_7$ | C—(CH$_3$)$_3$ | H | H | 1 | 89 |
| iso-C$_3$H$_7$ | CH$_2$—C—(CH$_3$)$_3$ | H | H | 1 | 68 |
| iso-C$_3$H$_7$ | n-C$_4$H$_9$ | H | H | 2 | 84.5 |
| iso-C$_3$H$_7$ | C—(CH$_3$)$_3$ | H | H | 2 | 43.3 |
| iso-C$_3$H$_7$ | CH$_2$—C—(CH$_3$)$_3$ | H | H | 2 | 39 |
| n-C$_4$H$_9$ | CH$_2$—C—(CH$_3$)$_3$ | H | H | 1 | 87 |
| n-C$_4$H$_9$ | n-C$_3$H$_7$ | H | H | 2 | 83.4 |
| n-C$_4$H$_9$ | iso-C$_3$H$_7$ | H | H | 2 | 78 |
| n-C$_4$H$_9$ | n-C$_4$H$_9$ | H | H | 2 | 76.4 |
| n-C$_4$H$_9$ | C—(CH$_3$)$_3$ | H | H | 2 | 70 |
| n-C$_4$H$_9$ | CH$_2$—C—(CH$_3$)$_3$ | H | H | 2 | 71.4 |
| n-C$_4$H$_9$ | C—(CH$_3$)$_3$ | H | OCH$_3$ | 2 | 85.2 |
| ⌬ | C—(CH$_3$)$_3$ | H | H | 2 | 80.4 |
| Butoprozine | | | | | 70.4 |

| R | R$_1$ | X$_1$ | n | Dose | Maximal contracting effect (%) |
|---|---|---|---|---|---|
| iso-C$_3$H$_7$ | iso-C$_3$H$_7$ | H | 2 | $10^{-6}$ M | 26.5 |
| | | | | $10^{-7}$ M | 68.7 |

II. Haemodynamic Properties

In the dog, the compounds of the invention, administered intravenously in a dose of 5 mg to 10 mg/kg, reduce cardiac frequency by 15% to 40% and cause a slow progressive drop in arterial pressure. Furthermore, tests carried out, also on the dog, at a dose of 5 mg/kg administered intravenously in accordance with the method described in British Pat. No. 1,518,443 have shown that the compounds of the invention possess, on the whole, only slight α-antiadrenergic properties, generally lower than 50% and are devoid or almost devoid of β-antiadrenergic properties. Butoprozine, on the other hand, exerts under the same conditions, an α-antiadrenergic action far greater than 50% and a β-antiadrenergic action of about 50%. Compared to butoprozine the compounds of the invention present, therefore, a range of antiadrenergic activities which is much more restricted and some of the compounds do not have any such activities at all. At the same time, the compounds of the invention have been found to possess calcium-antagonistic properties similar to those of butoprozine.

It will be appreciated that for therapeutic use the compounds of the invention will normally be administered in the form of a pharmaceutical or veterinary composition which may be in a dosage unit form appropriate to the desired mode of administration.

Thus the pharmaceutical or veterinary composition may be in a dosage unit form suitable for oral administration, for example a coated or uncoated tablet, a hard- or soft-gelatin capsule, a packaged powder or a suspension or syrup. The composition may alternatively take the form of a suppository for rectal administration or of a solution or suspension for parenteral administration.

When in a dosage unit form, the compositions may contain, for example, from 15% to 50% of active ingredient by weight for oral administration, from 3% to 15% of active ingredient for rectal administration and from 3% to 5% of active ingredient for parenteral administration.

Irrespective of the form which they may take, the pharmaceutical or veterinary compositions of the invention will normally be prepared by associating at least one of the compounds of formula I or a pharmaceutically acceptable acid addition salt thereof with an appropriate pharmaceutical carrier or excipient therefor, for example one or more of the following substances: milk, sugar, starches, talc, magnesium stearate, polyvinylpyrrolidone, alginic acid, colloidal silica, distilled water, benzyl alcohol or flavouring agents.

The following non-limitative Examples illustrate the invention:

EXAMPLE 1

Preparation of 2-ethyl-3-[4-(3-tert-butylamino-propyl)-oxy-benzoyl]-indolizine acid oxalate A solution comprising 4.2 g (0.11 mol) of 2-ethyl-3-[4-(3-bromo-propyl)oxy-benzoyl]-indolizine and 2.4 g (0.033 mol) of tert-butylamine in 40 ml of toluene was heated at 50° C. for 50 hours in a flask. At the end of the reaction, the mixture was allowed to cool and was then poured into 40 ml of water and alkalinized with an aqueous solution of 10% sodium hydroxide. The organic phase was separated out and the aqueous solution extracted with toluene. The organic phases were combined and washed with water to neutrality. The resulting solution was evaporated to dryness and the oily residue was purified by elution chromatography over aluminium oxide using 1,2-dichloroethane as eluent.

The purified oil product was dissolved in ethyl ether and an ethereal solution of anhydrous oxalic acid was added and the solid product obtained was recrystallized in methanol.

In this way, 3.9 g of 2ethyl-3-[4-(3-tert-butylamino-propyl)-oxy-benzoyl]-indolizine acid oxalate were obtained.

Yield: 75%.

M.P.: 207–208° C.

In accordance with the method described above the following compounds were prepared:

2-Ethyl-3-[4-(3-ethylamino-propyl)-oxy-benzoyl]-indolizine acid oxalate
M.P.: 184° C. (ethanol).

2-Ethyl-3-[4-(3-n-butylamino-propyl)-oxy-benzoyl]-indolizine acid oxalate
M.P.: 155° C. (ethyl acetate/methanol).

2-n-Butyl-3-[4-(3-tert-butylamino-propyl)-oxy-benzoyl]-indolizine acid oxalate
M.P.: 110° C. and 143–145° C. (methanol/ethyl ether).

2-n-Butyl-3-[4-(3-n-butylamino-propyl)-oxy-benzoyl]-indolizine acid oxalate
M.P.: 167–168° C. (methanol/ethyl ether).

2-Ethyl-3-[4-(3-n-butylamino-propyl)-oxy-benzoyl]-indolizine acid oxalate
M.P.: 172–174+ C. (isopropanol).

2-Isopropyl-3-[4-(3-n-butylamino-propyl)-oxy-benzoyl]-indolizine acid oxalate
M.P.: 168–170° C. (ethanol).

2-Isopropyl-3-[4-(3-tert-butylamino-propyl)-oxy-benzoyl]-indolizine acid oxalate
M.P.: 195–197° C. (ethyl acetate/methanol).

2-Isopropyl-3-[4-(3-tert-butylamino-propyl)-oxy-benzoyl]-indolizine hydrochloride
M.P.: 238° C. (ethyl acetate/methanol).

2-Phenyl-3-[4-(3-n-butylamino-propyl)-oxy-benzoyl]-indolizine acid oxalate
M.P.: 210°–211° C. (dimethylformamide).

2-Phenyl-3-[4-(3-tert-butylamino-propyl)-oxy-benzoyl]-indolizine acid oxalate
M.P.: 205° C. (methanol/ethyl ether)

2-n-Butyl-3-[4-(3-methylamino-propyl)-oxy-benzoyl]-indolizine acid oxalate
M.P.: 132° C. (methyl ethyl ketone/methanol).

2-n-Butyl-3-[4-(2-tert-butylamino-ethyl)-oxy-benzoyl]-indolizine acid oxalate
M.P.: 205°–208° C. (methanol/ethyl ether).

2-Ethyl-3-[4-(3-neopentylamino-propyl)-oxy-benzoyl]-indolizine acid oxalate
M.P.: 210° C. (dimethylformamide).

2-n-Butyl-3-[4-(3-n-propylamino-propyl)-oxy-benzoyl]-indolizine acid oxalate
M.P.: 155°–157° C. (isopropanol).

2-n-Butyl-3-[4-(3-ethylamino-propyl)-oxy-benzoyl]-indolizine acid oxalate
M.P.: 171°–172° C. (methanol).

2-n-Butyl-3-[4-(3-isopropylamino-propyl)-oxy-benzoyl]-indolizine acid oxalate
M.P.: 159°–160° C. (isopropanol).

2-n-Butyl-3-[4-(3-neopentylamino-propyl)-oxy-benzoyl]-indolizine acid oxalate
M.P.: 190°–191° C. (methanol).

2-n-Butyl-3-[4-(2-neopentylamino-ethyl)-oxy-benzoyl]-indolizine acid oxalate
M.P.: 197°–198° C. (methanol).

2-Isopropyl-3-[4-(2-tert-butylamino-ethyl)-oxy-benzoyl]-indolizine hydrobromide
M.P.: 222° C. (ethanol/ethyl ether 2/1).

2-Isopropyl-3-[4-(2-neopentylamino-ethyl)-oxy-benzoyl]-indolizine acid oxalate
M.P.: 205°–207° C. (methanol).

2-Isopropyl-3-]4-(3-neopentylamino-propyl)-oxy-benzoyl]-indolizine acid oxalate
M.P.: 206°–207° C. (methanol).

2-Methyl-3-[4-(3-tert-butylamino-propyl)-oxy-benzoyl]-indolizine acid oxalate
M.P.: 215° C. (methanol).

2-n-Propyl-3-[4-(3-tert-butylamino-propyl)-oxy-benzoyl]-indolizine acid oxalate
M.P.: 182°–184° C. (methanol).

2-n-Propyl-3-[4-(3-neopentylamino-propyl)-oxy-benzoyl]-indolizine acid oxalate
M.P.: 190°–192° C. (methanol).

1-Chloro-2-n-butyl-3-[4-(3-tert-butylamino-propyl)-oxy-benzoyl]-indolizine acid oxalate
M.P.: 168° C. (ethanol).

1-Chloro-2-n-butyl-3-[4-(3-n-butylamino-propyl)-oxy-benzoyl]-indolizine acid oxalate
M.P.: (164° C. (ethanol).

1-Bromo-2-n-butyl-3-[4-(2-neopentylamino-ethyl)-oxy-benzoyl ]-indolizine acid oxalate
M.P.: 195°–197° C. (methanol).

1-Bromo-2-n-butyl-3-[4-(2-tert-butylamino-ethyl)-oxy-benzoly]-indolizine acid oxalate
M.P.: 220°–222° C. (methanol).

1-Bromo-2-n-butyl-3-[4-(3-tert-butylamino-propyl)-oxy-benzoyl]-indolizine acid oxalate
M.P.: 168°–170° C. (methanol).

1-Bromo-2-n-butyl-3-[4-(3-neopentylamino-propyl)-oxy-benzoyl]-indolizine hydrobromide
M.P.: 184°–186° C. (methyl ethyl ketone/methanol).

1-Bromo-2-phenyl-3-[4-(3-n-butylamino-propyl)-oxy-3-chloro-benzoyl]-indolizine acid oxalate
M.P.: 176°–178° C. (methanol).

1-Bromo-2-isopropyl-3-[4-(3-tert-butylamino-propyl)-oxy-benzoyl]-indolizine hydrochloride
M.P.: 207°–209° C. (ethyl ether/methanol 9/1).

2-n-Butyl-3-[4-(3-tert-butylamino-propyl)-oxy-3-methoxy-benzoyl]-indolizine acid oxalate
M.P.: 168° C. (ethanol).

2-Isopropyl-3-[4-(3-tert-butylamino-propyl)-oxy-3,5-dimethyl-benzoyl]-indolizine acid oxalate
M.P.: 244° C. (methanol).

2-Isopropyl-3-[4-(3-tert-butylamino-propyl)-oxy-3-bromo-benzoyl]-indolizine hydrochloride
M.P.: 238° C. (methanol/ethyl ether).

EXAMPLE 2

In accordance with known pharmaceutical techniques a hard-gelatin capsule was prepared containing the following ingredients:

| Ingredient | mg |
| --- | --- |
| Compound of the invention | 100.0 |
| Starches | 99.5 |
| Colloidal silica | 0.5 |
| | 200.0 |

We claim:
1. An indolizine derivative corresponding to the general formula:

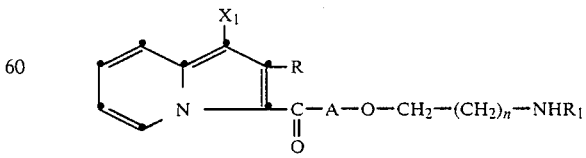

or a pharmaceutically acceptable acid addition salt thereof, wherein:
R respresents straight- or branched-chain alkyl having from 1 to 4 carbon atoms or phenyl, $R_1$ represents straight- or branched-chain alkyl having from 1 to 6 carbon atoms, $X_1$ represents hydrogen, chlorine, bromine, methyl or methoxy, A represents a radical of the formula:

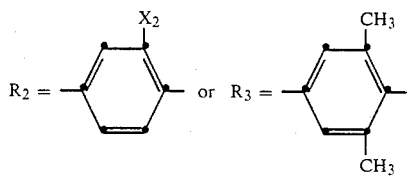

in which $X_2$ represents hydrogen, chlorine, bromine, methyl or methoxy n represents 1 or 2.

2. An indolizine derivative as claimed in claim 1 wherein the pharmaceutically acceptable acid addition salt is the hydrochloride, the hydrobromide or the acid oxalate.

3. 2-Isopropyl-3-[4-(3-tert-butylamino-propyl)-oxy-benzoyl]-indolizine or a pharmaceutically acceptable acid addition salt thereof.

4. 2-n-Propyl-3-[4-(3-tert-butylamino-propyl)-oxy-benzoyl]-indolizine or a pharmaceutically acceptable acid addition salt thereof.

5. 2-n-Propyl-3-[4-(3-neopentylamino-propyl)-oxy-benzoyl]-indolizine or a pharmaceutically acceptable acid addition salt thereof.

6. 2-Isopropyl-3-[4-(3-neopentylamino-propyl)-oxy-benzoyl]-indolizine or a pharmaceutically acceptable acid addition salt thereof.

7. 2-Isopropyl-3-[4-(3-tert-butylamino-propyl)-oxy-3-bromo-benzoyl]-indolizine or a pharmaceutically acceptable acid addition salt thereof.

8. An indolizine derivative as claimed in any one of claims 3 to 7 wherein the pharmaceutically acceptable acid addition salt is the hydrochloride, the hydrobromide or the acid oxalate.

9. 2-Isopropyl-3-[4-(3-tert-butylamino-propyl)-oxy-benzoyl]-indolizine hydrochloride.

10. A pharmaceutical or veterinary composition containing, as essential active ingredient, an effective amount for inhibiting calcium translocation at the level of the cell membrane of at least one indolizine derivative as claimed in claim 1 or 2 in association with a pharmaceutical carrier or excipient therefor.

11. A pharmaceutical or veterinary composition containing, as essential active ingredient, an effective amount for inhibiting calcium translocation at the level of the cell membrane of at least one indolizine derivative as claimed in any one of claims 3 to 7, or 9 in association with a pharmaceutical carrier or excipient therefor.

12. Method of inhibiting calcium translocation at the level of the cell membrane in a subject in need of such treatment which method comprises the administration to said subject of an effective dose of the composition of claim 10.

13. A method according to claim 12 wherein the effective dose is from 2 to 500 mg daily for a human being weighing 60 kgs.

* * * * *